United States Patent
Marquet et al.

(10) Patent No.: US 11,565,136 B2
(45) Date of Patent: Jan. 31, 2023

(54) SYSTEM FOR THE ABLATION OR THE MONITORING OF A ZONE OF THE HEART BY ULTRASOUNDS AND ASSOCIATED METHODS

(71) Applicants: UNIVERSITE DE BORDEAUX, Bordeaux (FR); INSTITUT NATIONAL DE LA SANTE ET DE LA RECHERCHE MEDICALE, Paris (FR); CENTRE HOSPITALIER UNIVERSITAIRE DE BORDEAUX, Talence (FR)

(72) Inventors: Fabrice Marquet, Bordeaux (FR); Pierre Bour, Talence (FR); Bruno Quesson, Bordeaux (FR); Fanny Vaillant, Bordeaux (FR)

(73) Assignees: UNIVERSITE DE BORDEAUX, Bordeaux (FR); INSTITUT NATIONAL DE LA SANTE ET DE LA RECHERCHE MEDICALE, Paris (FR); CENTRE HOSPITALIER UNIVERSITAIRE DE BORDEAUX, Talence (FR)

(*) Notice: Subject to any disclaimer, the term of this patent is extended or adjusted under 35 U.S.C. 154(b) by 654 days.

(21) Appl. No.: 15/508,193

(22) PCT Filed: Sep. 1, 2015

(86) PCT No.: PCT/EP2015/069968
§ 371 (c)(1),
(2) Date: Mar. 2, 2017

(87) PCT Pub. No.: WO2016/034594
PCT Pub. Date: Mar. 10, 2016

(65) Prior Publication Data
US 2017/0281983 A1    Oct. 5, 2017

(30) Foreign Application Priority Data
Sep. 2, 2014    (FR) .................................... 1458206

(51) Int. Cl.
*A61B 5/00* (2006.01)
*A61B 5/055* (2006.01)
(Continued)

(52) U.S. Cl.
CPC .............. *A61N 7/02* (2013.01); *A61B 5/0036* (2018.08); *A61B 5/055* (2013.01); *A61B 5/7285* (2013.01);
(Continued)

(58) Field of Classification Search
USPC ......................................... 600/411
See application file for complete search history.

(56) References Cited

U.S. PATENT DOCUMENTS

| 6,508,774 B1 * | 1/2003 | Acker ................ A61N 7/02 601/1 |
| 6,936,046 B2 * | 8/2005 | Hissong .............. A61N 7/02 601/2 |

(Continued)

FOREIGN PATENT DOCUMENTS

| CN | 101754784 A | 6/2010 |
| EP | 0 627 206 A2 | 12/1994 |
| EP | 2 312 303 A1 | 4/2011 |

OTHER PUBLICATIONS

International Search Report as issued in International Patent Application No. PCT/EP2015/069968, dated Nov. 2, 2015.
(Continued)

*Primary Examiner* — Serkan Akar
*Assistant Examiner* — Amal Aly Farag
(74) *Attorney, Agent, or Firm* — Pillsbury Winthrop Shaw Pittman LLP (57) ABSTRACT

A system for ablating or monitoring a zone of the heart, includes a system to measure the heart electrical activity; a
(Continued)

phased array for generating a beam of focussed ultrasound signals on a targeted zone of the heart; an imaging system determining an image of a transcostal wall projected in an image plane of the phased array by taking into consideration a position and direction of the phased array and making it possible to deactivate elements of the phased array in accordance with the position of the elements with regard to the position of the projected image of the transcostal wall; a positioning system to control the position of a focussed zone of a beam of focussed ultrasound signals on the targeted zone, a monitoring system to measure a temperature and tissue deformation in the targeted zone; and a device for measuring a level of cavitation in the targeted zone.

10 Claims, 4 Drawing Sheets

(51) Int. Cl.

| | | |
|---|---|---|
| *A61B 8/00* | (2006.01) | |
| *A61B 8/08* | (2006.01) | |
| *A61B 90/00* | (2016.01) | |
| *A61N 7/02* | (2006.01) | |
| *A61B 34/10* | (2016.01) | |
| *A61B 18/00* | (2006.01) | |
| *A61B 17/00* | (2006.01) | |
| *A61B 6/00* | (2006.01) | |
| *A61B 5/318* | (2021.01) | |

(52) U.S. Cl.
CPC ............ *A61B 8/085* (2013.01); *A61B 8/0883* (2013.01); *A61B 8/543* (2013.01); *A61B 34/10* (2016.02); *A61B 90/37* (2016.02); *A61B 5/318* (2021.01); *A61B 6/503* (2013.01); *A61B 6/541* (2013.01); *A61B 2017/00044* (2013.01); *A61B 2018/00351* (2013.01); *A61B 2018/00648* (2013.01); *A61B 2018/00702* (2013.01); *A61B 2018/00779* (2013.01); *A61B 2018/00791* (2013.01); *A61B 2018/00839* (2013.01); *A61B 2034/105* (2016.02); *A61B 2034/107* (2016.02); *A61B 2090/374* (2016.02); *A61B 2090/378* (2016.02); *A61B 2090/3762* (2016.02)

(56) References Cited

U.S. PATENT DOCUMENTS

| | | | |
|---|---|---|---|
| 2003/0117136 A1 | 6/2003 | Wang et al. | |
| 2004/0034301 A1* | 2/2004 | Falco | A61N 5/1049 600/427 |
| 2006/0005265 A1 | 1/2006 | Bughrara et al. | |
| 2006/0052695 A1* | 3/2006 | Adam | A61N 7/00 600/437 |
| 2006/0052701 A1 | 3/2006 | Carter | |
| 2007/0161902 A1* | 7/2007 | Dan | A61B 8/481 600/458 |
| 2008/0249395 A1* | 10/2008 | Shachar | A61B 5/062 600/409 |
| 2008/0269607 A1* | 10/2008 | Ishida | A61N 7/02 600/439 |
| 2009/0270730 A1 | 10/2009 | Azuma et al. | |
| 2010/0208957 A1* | 8/2010 | Chen | G06T 7/0016 382/128 |
| 2012/0165652 A1* | 6/2012 | Dempsey | A61B 90/37 600/411 |
| 2012/0172867 A1* | 7/2012 | Ryu | A61B 18/1206 606/41 |
| 2013/0150756 A1 | 6/2013 | Vitek et al. | |
| 2013/0184697 A1 | 7/2013 | Han et al. | |

OTHER PUBLICATIONS

Office Action as issued in Chinese Patent Application No. 2015800581623, dated May 12, 2020.

Non-Final Office Action as issued in U.S. Appl. No. 15/508,215, dated Jul. 2, 2021.

Non-Final Office Action as issued in U.S. Appl. No. 15/508,215, dated Oct. 29, 2021.

Mougenot, C., et al., "Three-Dimensional Spatial and Temporal Temperature Control With MR Thermometry-Guided Focused Ultrasound (MRgHIFU)," Magnetic Resonance in Medicine, vol. 61, pp. 603-614, (2009).

Final Office Action as issued in U.S. Appl. No. 15/508,215, dated Jul. 13, 2022.

* cited by examiner

SYSTEM FOR THE ABLATION OR THE MONITORING OF A ZONE OF THE HEART BY ULTRASOUNDS AND ASSOCIATED METHODS

CROSS-REFERENCE TO RELATED APPLICATIONS

This is the U.S. National Stage of PCT/EP2015/069968, filed Sep. 1, 2015, which in turn claims priority to French Patent Application No. 1458206, filed Sep. 2, 2014, the entire contents of all applications are incorporated herein by reference in their entireties.

FIELD

The field of the invention relates to methods for monitoring a beam of focussed ultrasound signals to establish a calibration of said beam and to establish an active monitoring during an ablation operation of diverse regions of the heart. Moreover, the field of the invention relates to methods of ablation from ultrasound signals. Furthermore, the field of the invention pertains to systems enabling the implementation of the processes of the invention.

PRIOR ART

Today, different solutions exist making it possible to treat cardiac rhythm disorders, known as "cardiac arrhythmias". One solution for treating certain zones causing cardiac dysfunctions is to conduct an ablation of the latter.

The ablation of a zone of an organ may be carried out by an intracardiac catheter introduced into the organ. In this specific case, the operation is followed from an imaging system in order to guide the ablation operation. When this operation is conducted in the heart, a drawback is that it requires considerable precautions to maintain the intervention environment sterile. Moreover, this method requires different single-usage catheters and thus has a significant cost at each intervention. Moreover, this latter operation includes risks and the monitoring of the zone to ablate is difficult to implement.

Another more recent solution is the ablation of a zone of an organ using extracorporeal means. One solution consists, for example, in using signals at a certain power and which interfere to create a heating zone in order to burn the cells or tissues of the organ.

This solution may be calibrated when the organ is relatively stable. On the other hand, this solution is much more difficult to implement and guide when the operation takes place on a moving organ. The operation becomes particularly sensitive and potentially dangerous if monitoring is not carried out. This is the case notably of an ablation on a zone of the heart. Indeed, since the heart is in movement, it is difficult to destroy defective cardiac tissue with the certainty of not damaging neighbouring non-defective tissue. In particular, the use of an ultrasound wave generator requires focusing a beam in a region of the heart while avoiding the bones of the ribs. Today, the solutions evoked in the prior art do not make it possible to carry out an ablation without causing damage to the transcostal wall.

The use of ultrasound signals for the ablation of certain zones of the heart causing a dysfunction is thus, at this stage, difficult to manage. Indeed, monitoring of the ultrasound signal generated is indispensable to determine and treat with precision the region to be treated and thus avoid any undesirable damage to regions bordering the zone to ablate.

To this end, the patent US no 2006/005265 pertains to cardiac stimulation by ultrasounds monitored by the coupling of an electrocardiograph measuring the electrical activity of the heart with an imaging system. This patent application notably evokes the possibility of carrying out an ablation by means of an ultrasound beam by locally heating the tissues in order to destroy them.

On the other hand, this solution remains silent as regards the monitoring necessary for the implementation of such an ablation process to avoid causing any thermal or mechanical damage beyond the zone concerned by the ablation.

Another solution disclosed in patent application US 2013/0184697 makes it possible to carry out an ablation of a zone of the heart by means of ultrasound signals. The application describes in particular how to detect electrically defective zones causing cardiac arrhythmias from a matrix of electrodes arranged on the patient. An electrical mapping of a region comprising the heart is carried out in order to detect electrically defective zones. This solution imposes the resolution of an inverse problem of measurements of electrical activities on a set of electrodes in order to reconstitute the electrical mapping of the heart. This method thus requires a long calibration of electrodes on a patient and a significant calculation cost to detect zones causing cardiac arrhythmias.

This method indicates that a monitoring of the temperature may be carried out, but it does not enable monitoring in real time of certain parameters before or during the ablation enabling the ablation operation to be made safe and to limit damage that could be caused to a zone concomitant to the zone concerned by the ablation.

SUMMARY OF THE INVENTION

The invention aims to overcome the aforementioned drawbacks.

The invention aims to propose a method for monitoring parameters making it possible to calibrate and guide the ablation operation in complete safety. Moreover, the invention relates to an ablation process comprising an active and dynamic monitoring of the ablation zone in such a way as to verify the operation is compliant with the expected precision. Moreover, the ablation process of the invention makes it possible to adjust dynamically the characteristics of a beam, power, deflection and duration, automatically as a function of a parameter monitored before or during the ablation operation.

The method of the invention is indifferently called method or process.

A subject matter of the invention relates to a method for monitoring a zone of the heart. The method comprises:
- an acquisition of the rhythm of the electrocardiogram of the heart;
- an acquisition of at least one image of a region of the heart in which a targeted zone is located, said at least one image being acquired in synchronisation with the rhythm of the electrocardiogram of the heart by an imaging system;
- a generation of a first beam of focussed ultrasound signals focussed in the targeted zone, said beams being emitted by a phased array, said signals being configured in phase to generate at least one pulse in a focussed zone, said at least one pulse being synchronised with the rhythm of the electrocardiogram of the heart, the pulse having a predefined amplitude and duration;
- a dynamic control of the position of the focussed zone on the position of the targeted zone by means of a positioning system, making it possible to measure respiratory movements of the heart in a reference frame linked to the phased array and to deduce therefrom a compensation parameter to calculate a new position of the targeted zone, said phased array automatically applying a phase parameter to each signal to deflect the beam to the new position of the targeted zone;

a determination of a temperature at the level of the focussed zone from an acquisition of at least one image of said zone by means of an imaging system.

An advantage of such a method is to carry out a test on the targeted zone $Z_C$ in order to calibrate the beam of ultrasound signals while generating the suitable amplitude and duration during the ablation of a zone of the heart.

An advantage of such a method is to carry out a monitoring of certain parameters such as the temperature, tissue deformation or electrical activity in the targeted zone in order to calibrate the beam of ultrasound signals by generating the suitable amplitude and duration during the ablation operation.

According to an embodiment, the method comprises:
a determination of tissue deformation in the focussed zone in response to at least one pulse of the first focussed beam.

According to an embodiment, the method comprises:
a determination by an imaging system of the image of the transcostal wall projected in an image plane of the phased array by taking into consideration the position and the direction of the phased array;
a deactivation of the elements of the phased array in accordance with the position of said elements with regard to the position of the projected image of the transcostal wall.

According to an embodiment, the method comprises
a dynamic control of the deactivation and the activation of the elements of the phased array as a function of the calculation of each phase parameter applied to each of the signals.

According to an embodiment, the temperature in the focussed zone and the tissue deformation are determined by a single imaging system, said imaging system being an MRI imaging system, the data acquired by the MRI imaging system making it possible to deduce a local tissue deformation induced by the ultrasound pressure generated by the beam of ultrasound signals and a local rise in temperature induced by the energy generated locally by the beam of ultrasound signals.

According to an embodiment, a comparison of the position of the focussed zone determined by an imaging system and the position of the targeted zone determined by the positioning system generates at least one data to calibrate the elements of the phased array in such a way as to make a position of the focussed zone correspond with the position of the targeted zone.

According to an embodiment, the positioning system may notably be:
an MRI imaging system, the positions being calculated from image processing;
a positioning system comprising at least one emitter emitting ultrasound waves and a plurality of ultrasound sensors detecting the reflected waves, the positions being determined by triangulation.

According to an embodiment, the monitoring method comprises a calibration of a signal generated in the focussed zone by the definition of parameters comprising at least one level of the amplitude and a pulse duration as a function of at least one data among which:

a temperature set point in the focussed zone and/or and in the neighbouring zones and/or in the ribs of the transcostal wall,
a tissue deformation set point in the focussed zone, and/or
a level of cavitation set point in the focussed zone, and/or
a detection of movement of the focussed zone in a reference point linked to the phased array, and/or
an electrical activity set point in the focussed zone ($Z_F$).

According to an embodiment, the steps of the monitoring method are carried out in different targeted zones ($Z_C$) of the heart, the method further comprising, after the application of a beam of focussed signals ($F_{US}$):
a verification of different values representing either tissue deformations of each targeted zone ($Z_C$), or electrical levels measured near to or in each targeted zone ($Z_C$), said measured values being compared with given thresholds.

Another subject matter of the invention relates to a method for ablating a given zone of a heart by generation of a beam of focussed ultrasound signals, characterised in that it comprises:
an acquisition of the rhythm of the electrocardiogram of the heart;
a determination of at least one position of a targeted zone in the heart;
a generation of a beam of focussed ultrasound signals in the targeted zone, of which
an amplitude is continuous and is comprised in the range of values [1-100 MPa],
a duration of application of the focussed beam being applied over a period above 1 ms,
a control of the position of the focussed zone of the beam on the position of the targeted zone calculated in real time by means of a positioning system,
an active monitoring in real time of a temperature in the focussed zone or a zone neighbouring the focussed zone from an acquisition of image(s).

According to an embodiment, the duration of application of the focussed beam comprises at least one micro-interruption of a duration above 1 ms during which the step of active monitoring comprises at least one measurement of the elasticity of the tissue of the targeted zone.

According to an embodiment, the active monitoring comprises a measurement of a level of cavitation of the focussed zone by means of an ultrasound sensor detecting a spectrum of ultrasound frequencies in or near to the focussed zone, the level of cavitation being deduced from a spectral noise level.

According to an embodiment, the active monitoring comprises a measurement of the elasticity of the tissue deduced from a measurement of a relaxation time of the tissue:
either from an image of an MRI imaging system;
or from an image of an ultrasound imaging system by an elastometry measurement.

According to an embodiment, the measurement of the elasticity of the tissue of the targeted zone and/or the measurement of the level of cavitation automatically determines a data corresponding to the duration of the focussed beam to apply after the micro-interruption and/or to determine the time at which a next micro-interruption will be generated.

According to an embodiment, a dynamic control of the position of the focussed zone on the position of the targeted zone by means of a positioning system makes it possible to measure respiratory movements of the heart in a reference frame linked to the phased array and to deduce therefrom a first compensation parameter to calculate a new position of the targeted zone, said phased array automatically applying a phase parameter to each signal to deflect the beam to the new position of the focussed zone.

According to an embodiment, a dynamic control of the position of the focussed zone on the position of the targeted zone by means of a positioning system makes it possible to measure contraction movements of the heart during the occurrence of the QRS complex in a reference frame linked to the phased array and to deduce therefrom a second compensation parameter to calculate a new position of the targeted zone, said phased array automatically applying a phase parameter to each signal to deflect the beam to the new position of the focussed zone.

According to an embodiment, the positioning system makes it possible to predict the moments of the occurrence of the QRS complex corresponding to the contraction of the heart and to generate:
- a set point for stopping the emission of at least one beam for the duration of the contraction, and
- a set point for reactivating the controlled beam after the end of the contraction.

According to an embodiment, the ablation method comprises:
- a determination by an imaging system of an image of a transcostal wall projected in an image plane of the phased array, by taking into consideration the position and the direction of the phased array;
- a deactivation of the elements of the phased array when the signals emitted from said elements are capable of intercepting the projected image of the transcostal wall.

According to an embodiment, the active monitoring comprises:
- a dynamic control of the deactivation and the activation of the elements of the phased array in accordance with the position of the projected image of the transcostal wall on the elements of the phased array.

According to an embodiment, a second active monitoring of zones neighbouring the focussed zone is carried out, said second active monitoring including the measurement of the following parameters in real time:
- a temperature of at least one zone ($Z_V$) neighbouring the focussed zone, and;
- a tissue deformation in at least one zone ($Z_V$) neighbouring the focussed zone in response to at least one pulse of the first focussed beam, and/or;
- a level of cavitation in at least one zone ($Z_V$) neighbouring the focussed zone in response to at least one pulse of the first focussed beam.

According to an embodiment, the ablation method comprises beforehand:
- a calibration of a focussed beam after the execution of the monitoring method;
- said calibration making it possible to determine the following parameters:
  - an amplitude configured such that the acoustic pressure applied in the focussed zone is continuous and is comprised in the range of values [1-100 MPa];
  - a duration of application of the focussed beam being applied over a period greater than 1 ms being able to include micro-interruptions.

According to an embodiment, a method of ablation of a plurality of targeted zones of a heart by generation of a beam of focussed ultrasound signals at a plurality of points comprises beforehand:
- a multi-point calibration of a focussed beam after the execution of the monitoring method;
- a configuration of an array of elements to generate a plurality of beams in a plurality of focussed zones.

According to an embodiment, the monitoring method is applied successively to the ablation method to verify that a tissue deformation or an electrical activity in this zone is less than a predetermined threshold, said targeted zone of the heart then being indicated as "non-responding".

Another subject matter of the invention relates to a system for the ablation or the monitoring of a zone of the heart by ultrasounds, said system comprising:
- a means for measuring the electrical activity of the heart to acquire an electrocardiogram;
- a phased array for generating a beam of focussed ultrasound signals in at least one targeted zone of the heart;
- a positioning system coupled to the phased array in such a way as to control the position of at least one focussed zone of at least one beam of focussed ultrasound signals on the position of the at least one targeted zone;
- a monitoring system capable of measuring a temperature and a tissue deformation in the targeted zone;
- a device for measuring a level of cavitation in the targeted zone.

Advantageously, the system for the ablation or the monitoring of a zone of the heart by ultrasounds is capable of implementing the steps of the monitoring and ablation methods.

BRIEF DESCRIPTION OF THE FIGURES

Other characteristics and advantages of the invention will become clearer on reading the detailed description that follows, with reference to the appended figures, which illustrate.

DESCRIPTION

Definitions and Introduction of the Principle

Figure 1:
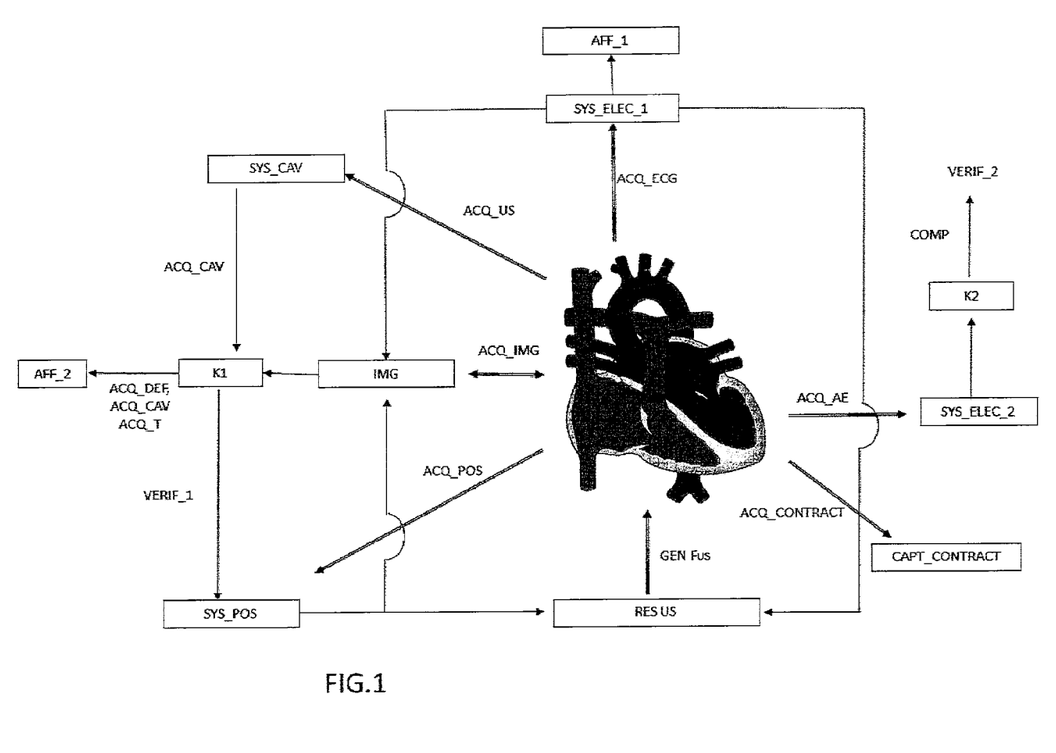
FIG. 1: a general operating diagram of the process of the invention.

FIG. 1 represents a general operating diagram of an embodiment of the process of the invention. The system of FIG. 1 represents different items of equipment that are described successively.

In the remainder of the description, the terms "amplitude" and "acoustic pressure" will be used indifferently.

A "pulse" may be interpreted at the level of the signal as an emission for a certain duration but also as the phenomenon induced locally by this signal. The induced phenomenon corresponds to a local ultrasound thrust resulting from an ultrasound radiation force. This latter thrust is capable of directly exerting a mechanical thrust on the cardiac tissues.

"Focussed beam" designates a set of signals coming from different elements of a phased array of which the frequency and phase characteristics make it possible to generate constructive or coherent interferences in a focussed zone.

The phased array makes it possible, according to the embodiments, to define one or more focussed zones in the heart thanks to a particular configuration of phases of each element of the phased array. The different focussed zones are obtained by making the signals of different elements of the phased array interfere at different points.

The process of the invention makes it possible to carry out measurements of monitoring parameters, such as tissue deformation ACQ_DEF, temperature ACQ_T, electrical activity ACQ_AE or instead the presence of a cardiac contraction ACQ_CONTRACT, during or consequent to the application of the focussed beam. Moreover, the processes of the invention make it possible to measure a level representative of the phenomenon of cavitation ACQ_CAV in or near to the focussed zone as well as a measurement of position or displacement ACQ_POS of the targeted zone $Z_C$. The measurement of displacements of the targeted zone $Z_C$ makes it possible for example to take into account respiratory movements or contractions of the heart in the control of the focussed beam.

The terms "tissue deformation" and "tissue displacement" are used indifferently in the description to describe the effect caused by the generation of an ultrasound thrust on the cardiac tissues.

A phased array RES_US makes it possible to generate one or more focussed beams in one or more focussed zones. Each focussed zone is controlled in position by a positioning system SYS_POS, for example ensured by means of an imaging system IMG or an intracardiac probe or potentially both.

The control of the position(s) of the beam(s) focussed at one or more point(s), called "focussed zone", is achieved by means of a position set point, called "targeted zone".

The mechanism for controlling the focussed beam on a targeted zone is advantageously synchronised between the positioning system and the phased array thanks to the acquisition of the ECG, which constitutes a time reference common to the different items of equipment.

A particularity of the process of the invention makes it possible to take into account a parameter of displacement of the position set point of the targeted zone caused by respiratory movements and/or the contraction of the heart to control suitably the phased array. A new targeted position is then calculated by means of a computer coupled to the positioning system to adapt the position set point to the phased array.

According to the process of the invention, the phased array is capable of generating a phase parameter to each signal emitted by an element of the array to deflect the beam and control the focussed point $Z_F$ on the new position of the targeted zone $Z_C$.

Furthermore, apart from respiratory phenomena, contraction movements of the heart subsist, particularly during the QRS complex of the ECG. In order to be free of contraction movements of the heart in the control of the focussed zone on the targeted zone, the focussed beam may:
- either be interrupted during the appearance of the QRS complex visible on the ECG;
- or be completed by the application of a second deflection correction to compensate the displacement of the heart during the appearance of the QRS complex.

The invention makes it possible to implement the two solutions during the monitoring process or during the ablation process.

ECG Acquisition

A first step of the processes of the invention, noted ACQ_ECG, comprises the acquisition of an electrocardiogram, noted ECG, of a patient or an animal from a first electrical system noted SYS_ELEC_1. According to an embodiment, the electrocardiogram makes it possible to acquire the rhythm of the beatings of a heart, which is displayed on a display, noted AFF_1.

According to an embodiment, the acquisition of the ECG is carried out by placing electrodes on the surface of the body of a patient or an animal. This solution makes it possible to measure the electrical activity of a heart in a non-invasive manner. According to an alternative embodiment, the ECG may be acquired using twelve or sixteen derivations according to known modalities of layout and positioning of electrodes.

According to an embodiment, a specific catheter is positioned in a cavity of the heart for the measurement of a local electrical activity. In this case, the process of the invention also makes it possible to compare the electrical activities acquired by the electrical catheter and the device making it possible to obtain the ECG. This means is noted SYS_ELEC_2 in FIG. 1.

Synchronisation of Applications

Apart from its display, the ECG is used according to the process of the invention to synchronise different items of equipment together. The synchronisation of the different items of equipment makes it possible to generate actions in synchronisation in one or more regions of the heart.

The synchronised actions comprise notably:
- the ballistic: that is to say the control of the position of the focussed zone on the position of the targeted zone or by taking into account for example the frequency of contraction of the heart in the control of the ballistic or the stoppage of the emission of the beams. This synchronisation takes into account movements of the heart as well as, if necessary, the avoidance of the transcostal wall, and/or;
- the monitoring: that is to say the measurement of certain monitoring parameters during or consequent to the generation of the beam.

Synchronisation of the Beam

The generation of the beam is advantageously synchronised during depolarisation of the cardiac tissues. For the ventricle, the focussed beam is thus generated preferentially during the QT period of the ECG. Advantageously, this synchronisation limits the generation of a cardiac stimulation being able to cause depolarisation of the cardiac tissues and potentially a contraction of the heart during an ablation operation.

Synchronisation of the Imaging

As regards the acquisition of at least one image ACQ_IM, it is also preferentially synchronised with the ECG. That is to say that the image is acquired at given times of the ECG. The image acquisition times with regard to the ECG may be configured by an operator or may be automatically deduced as a function of a synchronisation set point.

In an embodiment, the generation GEN $F_{US}$ of a beam of focussed ultrasound signals in a targeted zone of the heart and the acquisition of images ACQ_IMG are synchronised together with the ECG. "Synchronised" from the point of view of the phased array is taken to mean the fact that the generation of the ultrasound beam GEN $F_{US}$ is triggered at a determined time of the ECG. This synchronisation makes it possible to cause a desired physiological effect in a zone of the heart by taking into consideration the state of polarisation of the cardiac tissue.

Acquisition of Images

A second step, noted ACQ_IMG, comprises the acquisition of at least one image of a region of the heart, by an imaging system noted IMG, in which a targeted zone $Z_C$ is located, noted ACQ_$Z_C$.

According to an embodiment, the acquisition of the image is carried out by means of an MRI imaging system. Based on the magnetic properties of atoms, the MRI imaging system consists in applying a magnetic field to the atomic nuclei then stimulating said atomic nuclei by radiofrequencies. The reconstitution of an image is then possible from the signal emitted during the relaxation phase and collected by electromagnetic sensors.

Advantageously, the MRI imaging system coupled with a computer K1 makes it possible to:
- define a position of a targeted zone $Z_C$ as a set point for controlling the phased array of focussed signals; the position of the targeted zone $Z_C$ may also be defined by another positioning equipment;
- deduce tissue deformation and/or a variation in tissue deformation near to or in the focussed zone, MRI in this mode is more commonly known as MRI-ARFI; MRI-ARFI makes it possible to measure the hardness or the elasticity of tissues following a rise in temperature in an identified zone;
- deduce a temperature and/or a variation in temperatures near to or in the focussed zone, MRI in this mode is more commonly known as MRI-T;
- determine the projection of the transcostal wall of a patient in the image plane of the phased array to activate or deactivate the elements of the phased array capable of causing damage to the bone wall by taking into consideration a parameter of deflection of the beam.

According to another embodiment, the invention comprises an acquisition of an image by means of an ultrasound imaging system. This system may be used in addition to an MRI imaging system or as a substitute thereof for tissue displacements measurements. An ultrasound imaging system, called echocardiography, is based on the emission of acoustic waves in the body. Said waves are reflected differently according to the type of anatomic structures encountered. The signal collected, corresponding to the echoes of the waves emitted, makes it possible to reconstitute an image of a part of the anatomy of a patient or an animal.

An ecographic imaging system may also be used as a substitute for an MRI system to measure the temperature in the focussed zone and/or in a zone neighbouring the focussed zone.

According to another embodiment, the acquisition of an image is carried out by means of an X-ray imaging system. This imaging system is based on the emission of X-rays on the tissues. The measurement of the attenuation of the X-rays by the tissues makes it possible to reconstitute images in 2D or 3D of anatomical structures such as for example the heart. This system may be used in addition to an MRI imaging system or as a substitute thereof for ballistic measurements, that is to say the position of the focussed zone. The targeted zone $Z_C$ may be potentially defined from the imaging system.

According to another embodiment, the acquisition of an image is carried out by means of a positron emission imaging system (TEP), called tomoscintigraphy. This imaging system is based on the detection of gamma radiation emitted by a radioactive substance injected in small amounts into the body, which makes it possible to acquire images in section of certain organs such as for example the heart. This system may be used in addition to an MRI imaging system or as a substitute thereof for ballistic measurements, that is to say the position of the focussed zone and/or the targeted zone. The targeted zone $Z_C$ may be potentially defined from the imaging system.

The imaging systems may be, if need be, coupled with injected or ingested contrast agents, so as to improve the visualisation of the organs explored.

Positioning System

A positioning system is used during the execution of the processes of the invention to fulfil different functions:
- a first function is to define the position of a targeted zone that it is wished to reach. For this purpose, according to an example, the positioning system may be coupled to an imaging system to recover, on the image, the position ACQ_IMG of an identified targeted zone.
- a second function is to calibrate the ballistic of each device or system realising a function of the processes of the invention. Thus, the imaging systems and the phased array may be calibrated in position with a positioning system.
- a third function is control of the position of the focussed zone $Z_F$ on the position of the targeted zone $Z_C$. To do so, a set point is generated to the phased array so that the beam is correctly deflected.
- a fourth function is to generate a set point of activation or deactivation of the elements of the phased array in accordance with the projected position of the transcostal wall in the plane of the phased array. This function may be assured directly by the imaging system to the phased array. The use of the positioning system may make it possible to improve the speed of control without having to be limited by the acquisition time of the image. In the latter case, the calculations of the positions of the projected image of the transcostal wall may be memorised in the positioning system and changes in the positions of the patient may be calculated from a reference position.

According to an embodiment, the positioning system comprises extracorporeal ultrasound sensors and an extracorporeal emitter of which the emissions of ultrasound signals ACQ_US are reflected and detected by the sensors. A given position of the heart may be obtained by triangulation. Four sensors of signals make it possible to obtain good precision of the positions of zones in the heart. An advantage of this solution is that the control of a position in space may be quicker than by the use of an imaging system. Indeed, this solution requires less data to acquire and to process. The receptors acquire the variations on a line of the 3D space.

According to an alternative embodiment, the emitter is an emitter dedicated to the positioning system. According to another alternative embodiment, the emitter may be for example an element of the phased array notably to establish the calibration of the starting position.

The receptors of the phased array may be used. In order to improve measurement precision, ultrasound wave sensors dedicated to the positioning system are preferred.

In another embodiment, the positioning system is realised by means of sensors positioned on the skin.

When the position of the focussed zone $Z_F$ or the targeted zone $Z_C$ is determined from an imaging system IMG, according to an exemplary embodiment it may be recognised automatically from image processing. To this end, an indicator based on variations in parameters relative to the pixels of the image may be generated to recognise automatically a specific zone of the heart. According to another exemplary embodiment, the targeted zone $Z_C$ may be identified by means of an image processing tool with usage of a mouse or a graphic pointer. The targeted zone $Z_C$ may also be designated by the definition of space coordinates of a two-dimensional or three-dimensional image, for example from software configured to guide the phased array.

According to an embodiment, the position of the targeted zone $Z_C$ may be determined by means of an intracardiac catheter including an ultrasound or electromagnetic probe introduced into a ventricle or an auricle of the heart and coupled respectively to one or several ultrasound position sensors or to one or more electromagnetic position sensors. Said positioning system may thus be associated with an MRI imaging system or at least one ultrasound probe or instead at least one intracardiac sensor. An ultrasound probe makes it possible, according to an embodiment, to define the targeted zone $Z_C$ to control the position of the focussed beam and thus the focussed zone $Z_F$. This system may be used in addition to an MRI imaging system or as a substitute thereof for tissue displacement measurements.

The positioning system makes it possible to define a position of the targeted zones $Z_C$, which is transmitted to the phased array or to the generator of ultrasound signals in order to control it in position. Secondly and optionally, the positioning system is capable of recovering the position of the focussed zone $Z_F$ to deduce therefrom a difference with the position set point of the targeted zone. The positioning system may thus be integrated in an imaging system by a function implemented in a computer or be external to the imaging system and be associated therewith to extract data from the acquired image.

According to an embodiment, the process of the invention makes it possible to identify one or more targeted zones $Z_C$. This step makes it possible to fulfil different functions of which the control of the focussed zone $Z_F$, as described previously.

A function assured by the processes of the invention, according to an embodiment, comprises a comparison of imaging data of the targeted zone $Z_C$ or of a zone near to it before and after the emission of a monitoring pulse in the heart to determine a parameter of tissue deformation and/or a parameter of variation in temperature. Indeed, when a comparison of images is carried out, the process of the invention makes it possible to identify a gradient of values on the image, that is to say a variation translating for example a displacement of cardiac tissue and/or a variation in temperature. This is notably the case when the imaging system is an MRI imaging system and when it is coupled to a computer.

In FIG. 1, a step VERIF_1 makes it possible to monitor the calibration of the ballistic between the imaging system and the positioning system. This monitoring consists in verifying that the position of a point in space evaluated by one item equipment indeed corresponds to the position of a point in space evaluated by another item of equipment. After the application of a magnetic field, the latter makes it possible to deduce a dephasing parameter comprising a value relative to the displacement of the tissues and a value relative to the variation in temperature. The computer K1 makes it possible notably to conduct image processing operations to deduce monitoring parameters.

Phased Array, Generator of Signals

A third step, noted GEN $F_{US}$ comprises the generation of one or a plurality of beam(s) of focussed ultrasound signals $F_{US}$ focussed in the targeted zone(s) $Z_C$.

The therapeutic ultrasound probe is mounted on a 3D mechanical positioning system making it possible to locate the probe directly in line with the targeted cardiac region. Thanks to phased array technology, the ultrasound beam may be deflected electronically around the natural position of the focal point for a fine adjustment of the shot zone. This makes it possible to target easily different regions of the heart in order to carry out, for example, the simultaneous ablation of different regions of the heart.

According to an exemplary embodiment, a phased array with 256 elements may be used with a central frequency at 1 MHz. The geometric focus may be configured at 13 cm.

In an embodiment, the phased array of focussed ultrasound signals $F_{US}$ comprises a set of elements, such as elementary transducers. The configuration of the phased array enables the activation or the deactivation of the elements, and the parameterisation of the phases of each signal, which makes it possible to guide the deflection of the beam. The position of the focal point of the beam is thus determined by the parameterisation of the phases of each signal defining a given deflection. The configuration of the phased array makes it possible to take into account obstacles between the elements of the array and the heart, such as ribs or other organs. Thus, it is possible to configure the generation of one or several beam(s) while avoiding the obstacles. This makes it possible, for example, not to damage the ribs of a patient. The process of ablation of the invention is particularly efficient when the array is positioned facing the thoracic cage, the closest to the heart. In this configuration, the process of the invention makes it possible to establish a configuration of the phased array in order to avoid insonifying the ribs, burns being able to be induced by absorption of emitted ultrasound waves in a bone wall.

This configuration may be realised during the calibration of a focussed beam or during the ablation operation of at least one zone of the heart. The deflection of the beam may be controlled to compensate for respiratory movements or contractions of the heart inducing a displacement of the targeted zone. A new position of a targeted zone may be determined by an estimation of the displacement of this zone thanks to a positioning system as detailed previously.

The targeted zones $Z_C$ define a region in the reference frame of the heart and are thus capable of moving in a terrestrial reference frame. The phased array RES_US thus has to compensate for movements of the heart induced by respiratory movements or contractions of the heart. This is achieved thanks to the control of the focussed position $Z_F$ on the targeted position $Z_C$.

In particular, according to an embodiment, the deflection of the beam is controlled on a parameter of compensation of respiratory movements of the heart, Indeed, the respiratory movements generate displacements of the targeted zone $Z_C$ throughout the cardiac cycle and are preferentially compensated during the execution of the processes of the invention.

Optionally, according to an improved embodiment, the deflection of the beam may be controlled on a parameter of compensation of contraction movements of the heart occurring during the QRS complex. An alternative is to automatically switch off the beam during the appearance of the QRS complex to avoid, for example, during the process of ablation, damaging the tissues of a zone concomitant to the targeted zone $Z_C$ during a non-compensated movement of the heart. In this case, the extinction of the beam is controlled on the rhythm of the ECG so that the moments of appearance of the contraction, during the QRS complex, and the extinction of the beam, are synchronised.

Definition of Signals

In all the embodiments, the beam of focussed ultrasound signals $F_{US}$ is generated at a configured amplitude and for a configured duration so as to monitor the levels of mechanical and/or thermal damage to cardiac tissue to calibrate the levels of signals to apply during the ablation operation.

A calibration of signals according to the monitoring process of the invention may be carried out to prepare an ablation phase in which the signals define one or more optimised beams. The optimisation is carried out by calibrating the amplitude, the pulse duration, the number and the duration of the micro-interruptions as well as the repetition of the pulses of the focussed beam.

The beams generated by the monitoring process or the ablation process are advantageously generated such that the rising front of the pulse occurs during depolarisation of the cardiac tissues. Synchronisation with the ECG thus makes it possible to ensure the right moment to generate the focussed beam. The generation of the beam during depolarisation of the tissues makes it possible to avoid any stimulation of the tissues being able to induce a contraction of the heart or an electrical activity favouring such a contraction.

The calibration of the phased array RES_US depends on different criteria for monitoring and ablation: age, corpulence of the patient, size of the heart, thickness of the cardiac tissues, myocardium, stimulated zones, etc. The calibration of the phased array thus makes it possible to adapt a beam to define an efficient ablation.

The ablation may be carried out either by burning of cardiac tissue when the temperature rises beyond a threshold in the focussed zone, or by inertial cavitation, when the level of amplitude of the beam applied is above a given threshold.

When the ablation is carried out mainly by generating thermal damage to tissues leading to burning or necrosis of the tissues, the duration of the signal may be calibrated for a given amplitude of the beam.

When the ablation is carried out mainly by generating mechanical damage by the generation of a phenomenon of inertial cavitation, the amplitude of the beam has to be configured above a certain threshold.

During an ablation operation, the effects of thermal and mechanical damage most often appear jointly. The ablation process of the invention enables a configuration of the beams, making it possible to obtain a proportion of a given effect more significantly with regard to another effect.

According to an embodiment, the process of the invention comprises a step of injection of an ultrasound contrast agent into the organ, that is to say the heart.

According to a first embodiment, the ultrasound contrast agent makes it possible to visualise the ultrasound beams and to follow the treatment using an ultrasound imaging system. According to this embodiment, the ultrasound contrast agent may be used in combination with an ultrasound imaging device in the same way as a contrast agent is used to improve the visualisation of MRI images. This usage makes it possible for example to detect healthy zones and pathological zones.

This monitoring may be carried out:
before an operation of calibration of the focussed signals or before an ablation operation to prepare for the operation;
during these operations, for example to carry out an active monitoring of the signals in such a way as to regulate them or to stop the emission, or instead;
after operations, to verify for example that an ablation has indeed been carried out.

According to a second embodiment, the ultrasound contrast agent may be used to favour the action of the focussed ultrasound beam. The presence of the contrast agent makes it possible to improve the appearance of a phenomenon of cavitation when a signal is focussed by the generation of microbubbles. The appearance of this phenomenon being favoured, a consequence is to reduce the threshold of the maximums of amplitude of the acoustic signals enabling for example the ablation of a focussed zone of the heart. In this context, the contrast agent makes it possible to reduce the minimum thresholds of the levels of ultrasound signals used to ablate a zone of the heart. The ultrasound contrast agent thus makes it possible to reduce the power levels emitted by the beam generator while obtaining a result equivalent to that with a higher power without ultrasound contrast agent.

An interest of this solution is to reduce the emitted power levels and thus to reduce the risks of damage to tissues near to the zone to ablate. Another interest is to reduce damage caused to other organs or to bones by emissions of the beam.

A device that could be used may be for example that designated "SonoVue" from Bracco.

The administration of the ultrasound contrast agent may be injected over a wide range of values. Tests carried out on pig hearts have made it possible to validate the improvement of an ablation of a zone of 1 to 2 cm with lower acoustic pressure power levels when an ultrasound contrast agent was used. These data are of a same order of magnitude as those that can be obtained in humans. As an example, an injection ranging from 0.03 to 0.20 ml/kg of SonoVue may be used to obtain an effect of ablation of the tissues by application of a focussed beam. A value of 0.1 ml/kg leads to a conclusive result according to tests conducted with focussed acoustic signals of a power of 200 to 300 W for a duration of 10 to 20 s.

In this test, the half-life of terminal elimination was 12 minutes (ranging from 2 to 33 minutes).

The use of an ultrasound contrast agent makes it possible to obtain reductions in the power levels required in the focussed zone ranging from several hundredths of MPa to several MPa. The gains obtained depend on the quantity of ultrasound contrast agent administered, the period at which the beam is emitted after the administration of the contrast agent and physiological data of the organ specific to the patient or the animal.

Another advantage is that the effect of the ultrasound contrast agent is independent of the duration of the pulse of the beam, which guarantees a common operating mode. That is to say that it is possible to obtain the same amplification of the signals for different durations of pulses generated over the period during which the contrast agent produces an effect.

Monitoring of Parameters

In an embodiment, the phased array RES_US is configured in phase to generate a plurality of focussed beams and thus generate a plurality of pulses on several targeted zones $Z_C$. The multi-zone stimulation during the monitoring process of the invention makes it possible to observe the electrical responses and/or the deformations and/or the temperatures of said zones and thus to calibrate the beams to carry out an ablation. Comparisons of the responses make it possible to calibrate the focussed beam(s) used to schedule an ablation operation.

When an ablation is carried out on a plurality of targeted zones $Z_C$, it makes it possible to pool the operations and thus gain time.

In an embodiment, the beam of focussed ultrasound signals $F_{US}$ is configured to generate a pulse in a targeted zone $Z_C$ so as to stimulate the cardiac tissues in this zone. As specified above, the process of the invention makes it possible to analyse the electrical response and/or tissue deformation and/or temperature and/or level of cavitation in or near to said zone either before the ablation for the configuration of the beams, or during the ablation in order to monitor that the ablation is carried out correctly.

An advantage is to enable an automatic stoppage of an ablation underway when a monitoring error is detected. As an example, if an error is committed, for example on the ballistic, the ablation process may be automatically stopped. In this case, the process of the invention is capable of relaunching a calibration of the position of a targeted zone between the positioning system and the phased array RES_US.

Monitoring of the Temperature

The process of the invention makes it possible to monitor certain parameters such as the temperature ACQ_T at one or more zones of the heart for monitoring said zones during calibration or ablation operations. A display AFF_2 makes it possible in an embodiment to visualise in section or in 3D the temperatures of the heart or at least one particular region thereof. FIG. 1 represents a single display AFF_2 pooling the displays of different items of equipment. According to another embodiment, different displays may be used and dedicated to each item of equipment in the processes of the invention.

A computer, noted K1, makes it possible to extract data acquired by an imaging system IMG, such as an MRI, to deduce the temperatures in certain zones of the heart. An extraction of the position of the targeted zone or the focussed zone may be carried out to identify the temperature in this zone or near to it. For example, the computer K1 is capable of calculating variations in temperatures by an analysis of the data of the image acquired and to identify automatically the zones for which the variations exceed a temperature threshold. The positions of the focussed zones may thus be deduced automatically by processing of the data of the image acquired in MRI.

When the temperature measurements are carried out by an MRI imaging system, the intrinsic difference between the dephasing due to a change in temperature and that due to a local displacement makes it possible to discriminate temperature variations.

According to a first embodiment, the monitoring of the temperature may be carried out during the execution of the monitoring process of the invention to calibrate the focussed beam used during the ablation operation.

According to a second embodiment, the monitoring of the temperature may be carried out during the execution of the ablation process. In this case, the term "active monitoring" is used. This active monitoring notably makes it possible to follow the heating of the targeted zone to avoid overheating of zones in which the cardiac tissues must not suffer damage.

When the variations in temperatures are visible on the screen, a colour code may help an operator to avert significant temperature rises.

Monitoring of Electrical Activity

In an embodiment, a measurement of the local electrical activity, noted ACQ_AE, may be carried out during and/or after the generation of the beam of focussed ultrasound signals GEN $F_{US}$ in addition to the measurement of the temperature in such a way as to verify the efficiency of the ablation in the focussed zone and/or to verify that adjacent zones respond electrically.

According to an embodiment, the level of electrical activity may also be measured from an electrical catheter introduced into a region of the heart: ventricle or auricle. This makes it possible to verify that the zone does not comprise tissues that do not deform and which could nevertheless be electrically conducting.

According to other embodiments, other items of equipment may be used making it possible to measure electrical activity locally in or near to the focussed zone. This equipment is noted SYS-ELECT_2 in FIG. 1. It makes it possible to acquire the signal ACQ_AE translating a level of local electrical activity. A computer K2 may be added to the system. It enables the implementation of an embodiment of the invention, by comparing a level of electrical activity with a reference level or instead to reconcile the values of level of electrical activity with the measurement of tissue deformation ACQ_DEF. These correlations/comparisons of values are represented by the function COMP in FIG. 1, carried out for example by means of the computer K2. A message of state VERIF_2 makes it possible to end up with the result of the comparison. According to another embodiment of the invention, the functions of the computer K2 may be realised by the computer K1.

The electrical response times of each targeted zone $Z_C$ may also be measured.

The monitoring process of the invention makes it possible, from a calibration pulse, to define electrical stimulation thresholds making it possible to cause damage to tissues in order to necrotise or destroy them. It is possible to deduce a level of theoretical electrical activity generated as a function of the measured level of tissue deformation.

When the electrical activity of the focussed zone is less than a predetermined threshold, the focussed zone is then considered as "non-responding" and the ablation operation can end. When the focussed zone is considered as non-responding, the process of monitoring or active monitoring during the ablation process makes it possible to verify that the ablation of a zone generating an arrhythmia has gone well and is finished.

The monitoring process may favour a calibration making it possible to establish a correspondence rule between the levels of electrical activities and the levels of displacements of tissues measured during the application of a focussed beam in a given focussed zone. This calibration may also take into account the responses to temperatures in this zone. The correlation notably makes it possible to determine an indicator of mechanical-electrical activity of the cardiac tissue of a given targeted zone.

During the monitoring or ablation process, this calibration may make it possible to measure uniquely tissue deformation levels and deduce the electrical activity induced and to configure the beam with a suitable amplitude and duration to conduct the ablation of the targeted zone.

When the measurement of tissue deformation, or a characteristic specific to their elasticity, is low, or even zero, then it is possible to deduce that no electrical activity is generated. The processes of the invention may thus advantageously be non-invasive. It may be noted that local electrical activity ACQ_AE in the targeted zone may be monitored and deduced from the ECG obtained, for example by means of electrodes. In this latter specific case, the electrical systems SYS_ELEC_1 and SYS_ELEC_2 of FIG. 1 may only form a single item of equipment. Notably, when a pulse is generated by the monitoring process of the invention and when a global depolarisation of a ventricle or an auricle takes place, then the electrical activity induced by the monitoring process is visible on an ECG by the presence of a peak. In this case, an electrical catheter may potentially be used to correlate the measurements of electrical activities deduced from the ECG or to obtain more precise measurements.

These means may make it possible to detect rapidly zones assumed non-responding, which are then tested locally electrically or mechanically.

Monitoring for the Presence of Cardiac Contraction

Finally, the monitoring and ablation processes of the invention may comprise a step of verification of the presence of a cardiac contraction. The verification of a mechanical contraction may be carried out by means of a blood pressure probe for example by a measurement of the heart pulse or by an intra-aortic probe for measuring the contraction of the heart. This equipment for measuring mechanical contraction is noted CAP CONTRACT in FIG. 1 and the measurement is noted ACQ_CONTRACT.

Monitoring of Cavitation

According to an embodiment, the monitoring process as well as the ablation process of the invention comprise a step of calculating a level of cavitation in the focussed zone. The phenomenon of cavitation is based on the phenomenon of creation of bubbles in the focussed region generated by the vibration of the ultrasound waves emitted. Two cavitations that may occur may be distinguished:
- a stable cavitation, which corresponds to a phenomenon of creation of bubbles in the focussed zone or near to it. The bubbles potentially favour the displacement of tissues;
- an inertial cavitation, which is in the continuity of stable cavitation, in which the bubbles vaporise or burst, which can create damage to tissues but which can also stimulate the zone. The phenomenon of inertial cavitation is created by generation of a negative pressure locally beyond a certain threshold.

The phenomenon of cavitation may be determined by a device for measuring a level of cavitation. According to an exemplary embodiment, it may be an ultrasound device for the detection of a level of cavitation ACQ_CAV in or near to the focussed zone, noted SYS_CAV in FIG. 1. This device comprises a sensor or several sensors of ultrasound waves and a computer carrying out a spectral analysis ACQ_US of the ultrasound waves reflected in or near to the focussed zone.

According to an embodiment, a computer K1 makes it possible to centralise the different measurements carried out by different items of equipment of which the measurements of the level of cavitation ACQ_CAV, tissue deformation ACQ_DEF, temperature ACQ_T. The measurements are potentially compared to thresholds. Alarms may be generated according to predefined thresholds of these measurements being exceeded in real time. A display AFF_2 potentially makes it possible to display these values and the images acquired by the different items of equipment.

According to another embodiment, each item of equipment may be coupled to a dedicated computer and a dedicated display.

The more the spectrum is spread out, that is to say the higher the noise in or near to the focussed zone, the more the phenomenon of cavitation is determined as important. Thresholds may be defined and determined from the monitoring process of the invention for calibrating the values of amplitudes and durations of the signals used notably for the stimulation for the ablation. According to an embodiment, the active monitoring carried out during the process of ablation detects in real time a level representing the importance of the phenomenon of cavitation. The ablation process may dynamically take into account the measured levels:

either to stop the beam(s), if the level is too high,
or to configure automatically the level of pressure generated at the focal point by an amplitude set point of instead to configure the remaining duration of application of the beam.

According to a first embodiment, the ablation process is configured with a beam of which the amplitude is less than a first cavitation threshold and of which the duration is above the second. The amplitude levels of the beam may be configured for a pressure applied to the focal point of 2 to 5 MPa. In this embodiment, the ablation process is configured to avoid the formation of a phenomenon of stable cavitation, this phenomenon being able to favour the stimulation of the heart, which it is sought to avoid. Indeed, a danger of the stimulation of the heart during the ablation process is to favour the occurrence of electrical depolarisation, which can cause a problem of ballistic control for example. Thus, the ablation process of the invention comprises a configuration in which the targeted zone is damaged preferentially by the creation of thermal damage, that is to say thanks to pulses of long durations and with managed signal amplitudes.

The beam is preferentially generated before the T-wave, for example in the QT interval of the ECG. In this case, the beam advantageously does not create electrical stimulation in the targeted zone of the heart.

According to a second embodiment, the ablation process is configured with a beam of which the amplitude is high, from 1 to 100 MPa during pulses of short duration. The durations of application of the beam are of the order of several milliseconds corresponding to several cycles of ultrasound vibrations. A range of time values is from 1 ms to 50 ms. In a preferred embodiment, pulse durations of 5 ms to 10 ms make it possible to minimise the appearance of the phenomenon of stable and inertial cavitation. An example of amplitude of 8 to 12 MPa with pulses of 5 to 10 ms makes it possible to ablate a targeted zone while avoiding electrically stimulating the focussed zone.

In this embodiment, the ablation process is configured to avoid the formation of a phenomenon of inertial cavitation favouring the stimulation of the heart and damage to the cardiac tissues in or near to the targeted zone. Indeed, a danger of stimulation of the heart during the ablation process is to favour the occurrence of electrical depolarisation, which could cause a problem of ballistic control for example. Thus, the ablation process of the invention comprises a configuration in which the targeted zone is damaged preferentially by the creation of mechanical damage, that is to say by means of pulses of short duration with a considerable local radiation force intensity.

The beam is preferentially generated before the T-wave, for example in the QT interval of the ECG. In this case, the beam advantageously does not create electrical stimulation in the targeted zone of the heart.

In a third embodiment, the ablation process is carried out while managing the phenomenon of inertial cavitation causing damage to the tissues. Indeed, the ablation may be carried out by managing damage to the tissues created by the phenomenon of inertial cavitation. On the other hand, a risk of this embodiment is to generate a stimulation of a zone of the heart which can perturb the smooth progress of the ablation process, notably by the occurrence of a contraction of the heart causing a ballistic error. To limit this risk, the pulses are generated during depolarisation of the cardiac tissues, for example during the QT period of the ECG for the ventricle.

According to another embodiment, which can be combined with the preceding embodiments, a measurement of a level of cavitation is compared with a first threshold and a measurement of a tissue deformation is compared with a second threshold.

According to a first alternative embodiment, the thresholds may be thresholds that correspond to the detection of risks of damage to the tissues of a zone neighbouring the focussed zone. Indeed, during an ablation operation, it may be necessary to monitor and to ensure that zones bordering the ablation zone do not suffer damage. The exceeding of the threshold may thus indicate a risk of damage to a zone bordering the zone to ablate.

According to a second alternative embodiment, which may be combined with the first alternative embodiment when different zones are monitored, the thresholds may be thresholds that correspond to an indicator of necrosis, representing for example percentage necrosis of a zone to ablate. The exceeding of the threshold may thus indicate a remaining time for applying the focussed signal to finish the ablation.

An algorithm making it possible to take into account the risks of neighbouring damage or the level of necrosis of a zone to ablate makes it possible to generate a set point for stopping the ablation procedure, for example by automatically cutting off the ultrasound signal emitted. An interest is to reinforce the safety procedure governing an intervention aiming to ablate a zone while ensuring that the neighbouring zones remain healthy.

Finally, another interest resides in the possibility of obtaining a double indicator over time based on a double assessment by two different means, either of a risk of damage, or an indicator of necrosis. Indeed, an ultrasound sensor measuring the level of cavitation may acquire between 10 and 5000 signals per second, whereas a tissue deformation sensor, using for example MRI, will require an acquisition refresh rate of 0.5 to 10 signals per second. It is thus possible to have available a system comprising calculation means making it possible to carry out a first measurement of the level of cavitation and to compare this measurement with a threshold. A second measurement of a level of deformation may be carried out successively to the measurement of cavitation. The detection of the evolution of the level of deformation may be analysed in the time span succeeding the detection of the first risk identified. Hence, it is possible to bring about a cut off of the focussed signal as quickly as possible for reasons of safety if the monitored zone is a zone neighbouring the focussed zone or to carry out a simple measurement in the focussed zone to estimate the time remaining to finishing an ablation.

Furthermore, in the focussed zone or in a neighbouring zone, the first exceeding of the level of cavitation may lead to analysing the evolution of tissue deformation without all the same the second threshold being exceeded. The analysis then concerns the tendency of the tissues to deform and not the exceeding of a second given threshold. Thus, it is possible, thanks to the process of the invention, to cut off or to maintain the generation of the signal as a function of the analysis of the measurements.

According to an alternative, the measurement of the level of cavitation is no longer correlated with the measurement of tissue deformation but with the electrical activity in or near to the focussed zone. In this latter case, the same treatment may be applied to these two measurements, notably as regards the analysis of the signals by the different items of equipment over time.

The algorithm may also enable the generation of a cut off of the ultrasound signals uniquely when two thresholds are exceeded during a monitoring of a neighbouring zone. A first threshold concerns the level of cavitation and a second threshold concerns, for example, the deformation of the tissues. This option makes it possible to consider the measurement errors of one of the measurement apparatuses, such as the MRI or an ultrasound device for example.

The process of the invention thus makes it possible to define different strategies for monitoring a zone neighbouring a zone to ablate or the zone to ablate.

A first strategy may correspond to ensuring a maximum degree of safety. In this case, a single exceeding of a threshold in a neighbouring zone makes it possible to generate a cut off of the beam of signals, A second strategy corresponds to ensuring the elimination of measurement errors. In this case, the process makes it possible to confirm that damage occurs in a neighbouring zone if two thresholds of measurements of different items of equipment are exceeded.

It may be noted that the process applies with a plurality of measurements corresponding to quantities measured with different items of equipment. Thus, a correlation of three types of signals may be carried out by making comparisons with regard to three thresholds. For example, the level of cavitation is compared to a first threshold, tissue deformation is compared to a second threshold and electrical activity is compared to a third threshold. A strategy for monitoring a neighbouring zone may be that exceeding two thresholds out of three suffices to generate a cut off of the ultrasound signals. This solution enables a compromise between a gain in safety (2 apparatuses out of 3 have detected a risk) and taking into account measurement errors (1 apparatus out of 3 has detected nothing). Other possibilities may be decided depending on whether a configuration favouring maximum safety is desired: at least one threshold being exceeded leads to the cut off of the beam or depending on whether a configuration in which measurements errors are taken into account is desired: the three thresholds have to be exceeded to bring about a cut off of the beam.

Monitoring of Tissue Deformation

Tissue deformation may be measured locally during the execution of the monitoring process to verify the state of elasticity of the cardiac tissue. The tissue deformation may be used to assess the characteristics of the tissues of a zone causing a cardiac arrhythmia and thus to validate the ablation operation of the targeted zone.

The generation of the beam(s) of ultrasound signals GEN $F_{US}$ makes it possible to generate an ultrasound thrust localised in a focussed zone $Z_F$ and possibly substantially near to this zone by displacement of the tissues.

In the case of ablation, the measurement of the deformation of tissues locally serves to calibrate the pressure level by means of the monitoring process of the invention and to verify the ballistic without inducing a thermal effect.

Indeed, when the tissue deformation is located by an imaging system, either by MRI or by ultrasounds, it is possible to correlate the data of positions with those of the positioning system. Typically, the zones in which the elastic response of the tissues is compared with the position ACQ_POS of the targeted zone identified with the positioning system SYS_POS. This comparison also makes it possible to calibrate the positions located between the imaging system, MRI or ultrasound, and the phased array guided in position by the positioning system.

Finally, the measurement of the deformation of tissues makes it possible to calibrate the levels of elasticity of the tissue in a targeted zone during the ablation process to note that a coagulative necrosis has finished, for example, in the targeted zone. A comparison of the levels of elasticity during the ablation with a measurement carried out beforehand makes it possible to quantify the proportion of ablated zone as a function of a level to reach or instead to quantify the remaining duration of application of the beam.

Tissue deformations may be measured from an MRI imaging system as specified previously. Other imaging systems may be used when the latter make it possible to monitor deformation or elasticity of the tissue. According to another embodiment, tissue deformations may be measured by a catheter comprising an ultrasound probe introduced near to the focussed zone ($Z_F$) measuring tissue deformation. Optionally, a catheter comprising a pressure probe may be used near to the focussed zone to deduce tissue deformations.

The phenomenon of cavitation in the targeted zone may also be measured by the processes of the invention:
  either by extrapolation of tissue deformation essentially generated by this phenomenon;
  or by extracorporeal ultrasound sensors, as specified previously, by spectral analysis of the reflected signals;
  or by an intracardiac ultrasound sensor positioned near to the targeted zone.

Phenomenon of Destruction of Cardiac Tissues

Thus, the ablation process of the invention may be configured so as to generate damage to cardiac tissues in a focussed zone so as to necrotise or to burn them.

The damage may be caused:
  by a phenomenon of burning, by heating the tissues above a certain temperature threshold, for example with pulses of which the amplitude is limited and of which the duration of application is sufficiently long to produce heating of the zone considered,
  by a phenomenon of mechanical damage, by configuring very short pulses with high amplitudes,
  by a phenomenon of inertial cavitation obtained for a certain power or a given amplitude of the focussed beam.

The three phenomena may be combined so as to create thermal and mechanical damage and inertial cavitation in the cardiac tissues. The ablation process of the invention enables a configuration having the objective of managing damage linked to each phenomenon, notably to avoid:
  damaging neighbouring zones,
  damaging the targeted zones more than necessary,
  generating a cardiac stimulation during the ablation process, generating a cardiac contraction or modifying the cardiac frequency,
  loss of ballistic control, which can cause burning of zones other than that concerned by the ablation,
  burning the bones of the transcostal wall.

Tests have made it possible to validate the process of the invention on pig hearts, of a weight of 45 Kg+/−5 Kg, which were beating during the ablation operation. According to this example, a phased array comprising an array of 256 cells, that is to say 256 transducers, was used. A configuration was able to be obtained for a focal distance of 13 m and an opening of 13 cm. The emissions were produced in a magnetic field of 1.5 Tesla. According to this experiment, thanks to the process of the invention, it was tested that with a power of 300 W in the focussed zone with a pulse duration of 15 s, it was then possible to obtain an ablation of a zone of the heart of 1 to 2 cm$^3$. Such an ablation may be carried out inside the organ at several millimetres or centimetres from the myocardium wall. It may be observed that the maximum temperature rise was of the order of 21° C.+/−1.1° C. in or near to the focussed zone.

A plurality of zones of the heart may be ablated:
  either successively by a succession of pulses directed in different zones by calibrating a pulse duration substantially equal for each shot, or
  simultaneously when three focussed zones are aimed at by the phased arrays of the beam generator.

Figure 2A:
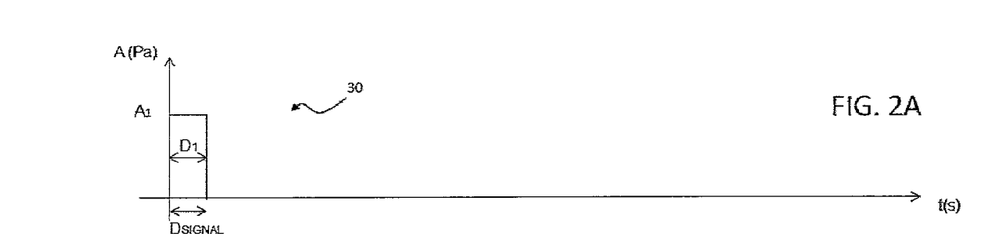
FIG. 2A: a diagram representing an example of stimulation of a targeted zone of the heart for calibrating a beam for an ablation application.
Figure 2B:
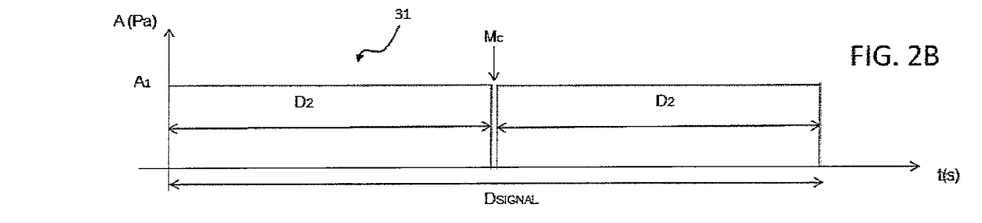
FIG. 2B: a diagram representing a first example of beam for the ablation of a targeted zone of the heart.
Figure 2C:
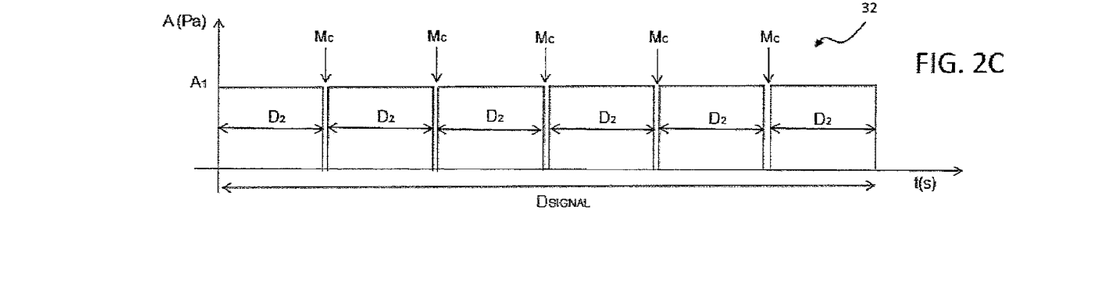
FIG. 2C: a diagram representing a second example of beam for the ablation of a targeted zone of the heart.

Description of FIGS. 2A to 2C

FIG. 2A is a diagram representing a pulse for the monitoring of a targeted zone. The pulse generated by the focussed beam $F_{US}$ at an amplitude $A_1$ and a duration $D_1$, the total duration of application being designated $D_{SIGNAL}$. The amplitude $A_1$ of the signal is representative of the ultrasound radiation force exerted on the tissues of the focussed zone.

The amplitudes $A_1$ and the durations $D_1$ of the pulses generated in the targeted zone $Z_C$ of the heart are chosen in such a way as to optimise mechanical and thermal damage while preserving bordering zones.

The pulse represented in FIG. 2A may be used for different purposes:
  a calibration of the beam to carry out an ablation operation without damaging zones neighbouring the targeted zone $Z_C$
  a calibration of the ballistic, making it possible to calibrate the phased array RES_US and the positioning system on a same position reference frame.

In an embodiment, a pulse is applied in a targeted zone $Z_C$ of the heart during repolarisation of the cardiac tissue during the step of monitoring for the calibration of the beam of ultrasound signals $F_{US}$ with the aim of measuring the electrical activity of the heart and/or the tissue deformation and/or the temperature induced by the pulse in the targeted zone $Z_C$ of the heart. According to the electrical response, the measured deformation and/or temperature, a calibration of the beam of ultrasound signals $F_{US}$ is carried out.

In another embodiment, a pulse is applied in a targeted zone $Z_C$ of the heart during depolarisation of the cardiac tissue for the monitoring of the ballistic without generating an extrasystole. This makes it possible to verify that the focussed zone $Z_F$ and the targeted zone $Z_C$ of the heart are merged or substantially close.

FIGS. 2B and 2C are diagrams, respectively 31 and 32, representing two examples of beams for the ablation of a targeted zone $Z_C$ of the heart. Said ablations are carried out by means of at least one beam of ultrasound signals $F_{US}$ applied at an amplitude $A_1$ and for a total duration of application $D_{SIGNAL}$. The total duration of application $D_{SIGNAL}$ comprises one micro-interruption, called $M_C$, in the beam of FIG. 2B, and five micro-interruptions in the case of the FIG. 2C.

In the embodiments 31 and 32, a focussed beam $F_{US}$ is configured such that the acoustic pressure $A_1$ in the focussed zone $Z_F$ is comprised in a pressure range of [1-10 MPa] for a total duration of application $D_{SIGNAL}$ comprised in the range of durations [1-120 s]. A longer duration may also be configured.

In this case, the duration of application of the signal is intersected by at least one micro-interruption $M_C$ comprised in the range of durations [1 ms-1 s]. The duration of application $D_{SIGNAL}$ being the sum of the durations $D_1$ and the duration of the micro-interruptions $M_C$. The duration of the micro-interruptions is configured to enable the carrying out of an active monitoring, for example by means of an MRI imaging.

In all the embodiments, the durations of the micro-interruptions $M_C$ are configured to carry out a monitoring of the targeted zone $Z_C$. Notably the mechanical and/or thermal damage to the focussed zone $Z_F$ may be deduced from a measurement of deformation of the tissues or electrical activity in the focussed zone. For example, these measurements, as specified previously, may be carried out by means of an MRI imaging system or by a catheter comprising an ultrasound probe or an electrical catheter.

A measurement of the deformation of the tissues makes it possible to deduce for example a measurement of the elasticity of the tissue or the duration of relaxation of the tissue or instead its contraction.

Moreover, a measurement of the temperature in the focussed zone makes it possible to evaluate the probable presence of thermal damage if the latter is above a predefined threshold indicating a probability of thermal damage.

In an embodiment, the evaluation of the levels of mechanical and/or thermal damage may be used to select the amplitude and the duration of application of the beam of ultrasound signals $F_{US}$ to continue the ablation of the targeted zone $Z_C$. Thus, following a micro-interruption $M_C$, the acoustic pressure or the duration during which the beam of ultrasound signals $F_{US}$ is applied may be adjusted by increasing or, on the contrary, by reducing said acoustic pressures and/or said durations of application up to the following micro-interruption $M_C$.

It is possible to choose shorter pulses and favour the appearance mainly of the phenomenon of cavitation to localise more precisely the damage during the end of the ablation. This solution makes it possible to reduce the duration of application of the beam in order to limit damage in zones bordering the targeted zone.

In all the embodiments, an active monitoring of the targeted zone $Z_C$ may be carried out by a measurement of the electrical activity and/or a measurement of the tissue deformation and/or a measurement of the temperature of the targeted zone $Z_C$ of the heart so as not to damage the targeted zone $Z_C$.

In all the embodiments, an active monitoring of zones neighbouring the focussed zone $Z_F$ may be carried out by a measurement of the electrical activity and/or a measurement of the tissue deformation and/or a measurement of the temperature of the zones neighbouring the targeted zone $Z_C$ of the heart so as not to damage the zones neighbouring the targeted zone $Z_C$.

Indeed, when the electrical activity and/or tissue deformation and/or temperature of the neighbouring zone(s) exceed(s) a predetermined threshold, the beam of ultrasound signals is configured to:
   either reduce the power of the beam, that is to say its amplitude, bringing about a reduction in the acoustic pressure, the appearance of the phenomenon of inertial cavitation and the temperature in the focussed zone,
   or suspend the beam automatically.

Figure 3:
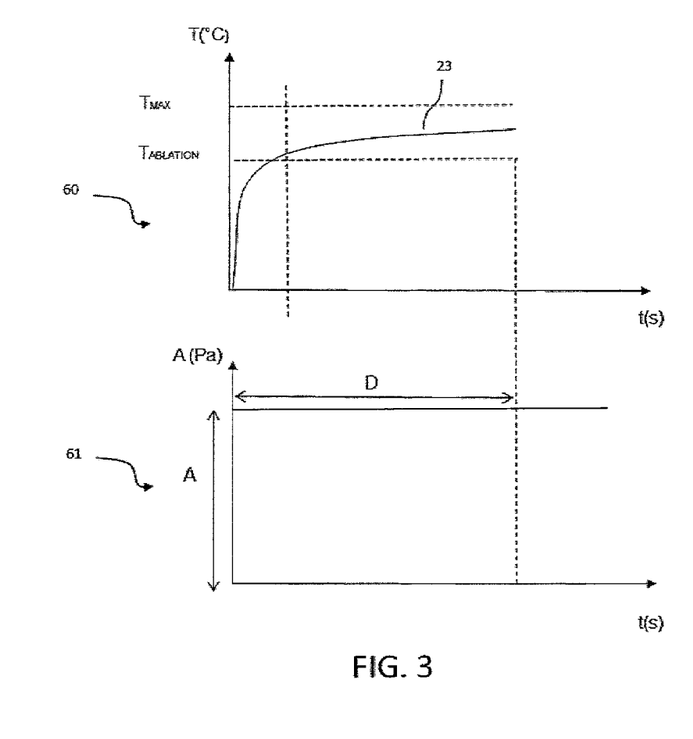
FIG. 3: diagrams representing the evolution of the temperature of the targeted zone as a function of an amplitude and a duration of application of a beam of ultrasound signals.

FIG. 3 comprises a graph representing the evolution of the temperature 60 of the targeted zone $Z_C$ as a function of time when a pulse 61 of amplitude A and of duration D is generated locally by the formation of a focussed beam $F_{US}$.

According to an embodiment, the beam of ultrasound signals $F_{US}$ is applied to a targeted zone $Z_C$ of the heart at an amplitude A comprised between [1-10 MPa] for a duration $D_{SIGNAL}$ above 1 s.

Advantageously, the duration of the signal is comprised between 1 s and 600 s. According to an embodiment, the duration of the signal is comprised between 1 s and 120 s. A number N of micro-interruptions may be programmed so as to deactivate the generation of the focussed beam during this period in such a way as to measure parameters of the tissues in the focussed zone and to carry out calculations.

At the end of the duration D of application of the beam, the measured temperature of the targeted zone $Z_C$ is monitored and maintained substantially at a temperature $T_{ABLATION}$. This temperature makes it possible to destroy or necrotise cardiac tissues in the focussed zone while remaining less than a temperature threshold $T_{MAX}$ for which destruction of neighbouring tissues is observed.

The monitoring process of the invention makes it possible, from the measurements carried out, to deduce the temperatures $T_{MAX}$ and $T_{ABLATION}$ for a given focussed beam. These latter deductions may be obtained by means of abacuses or correspondence tables between:
   on the one hand, a measured level of tissue deformation or a level of electrical activity observed during the monitoring process and,
   on the other hand, temperature levels measured in the focussed zone before the ablation observed during the monitoring process.

Figure 4:
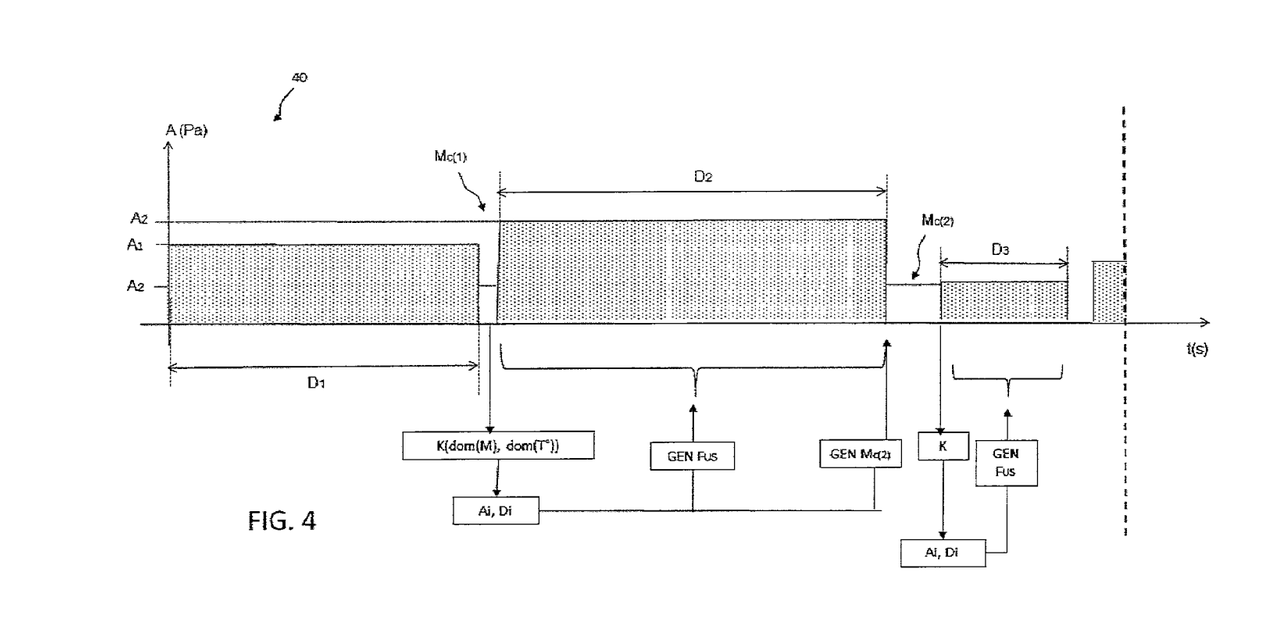
FIG. 4: a diagram representing a third example of beam for the ablation of a targeted zone of the heart.

FIG. 4 is a diagram representing an example of ablation of a targeted zone $Z_C$ of the heart by means of a focussed beam $F_{US}$ applied at amplitudes and for durations that are chosen as a function of the elasticity of the targeted zone $Z_C$ measured during the micro-interruptions $M_C(1)$, $M_C(2)$. Said micro-interruptions are of a duration above 1 ms. According to calculations carried out on certain parameters: temperature, tissue deformation, level of cavitation, the duration of the micro-interruption may be configured for a longer duration, for example 5 ms or 10 ms. Longer micro-interruptions may also be made.

In an embodiment, a first beam of ultrasound signals $F_{US}$ is generated at an amplitude $A_1$ for a duration $D_1$.

At the end of $D_1$, a first micro-interruption $M_C(1)$ is carried out during which a computer, noted K, connected to a system for measuring tissue deformation and temperature. As an example, a pressure probe and/or an imaging system may be used. The measurements of tissue deformation dom(M) and potentially temperature) dom(T°) of the tissues of the focussed zone $Z_F$ are determined for the calculation of a level of elasticity of the tissues in the focussed zone $Z_F$.

It may be noted that the computer of FIG. 4 may correspond, according to an embodiment, to the computer K1 of FIG. 1 when all the calculations are pooled on a single computer.

From the measurement of the elasticity of the tissues of said focussed zone $Z_F$, the computer K automatically determines a data corresponding to an amplitude $A_2$ and a duration of application $D_2$ for the application of a second focussed beam $F_{US}$ in the focussed zone $Z_F$. The generation of the beam by the phased array is noted GEN $F_{US}$ in FIG. 4.

In addition, the computer K1 may, advantageously, determine automatically the time at which a new micro-interruption $M_C(2)$ will take place according to the level of elasticity measured at the preceding micro-interruption $M_C(1)$.

In FIG. 4, the function of generation of a micro-interruption is noted GEN $M_C(2)$.

At the end of the duration $D_2$ of the second pulse of the focussed beam, a micro-interruption $M_C(2)$ may be carried out to measure again parameters relative to the properties of the tissues in the focussed zone $Z_F$. In this example, the second micro-interruption $M_C(2)$ is longer than the first micro-interruption $M_C(1)$. According to an embodiment, a measurement of the level of cavitation is carried out during this second micro-interruption $M_C(2)$.

For example, this latter measurement of cavitation may be guided:

by a measurement of the temperature during the first micro-interruption $M_C(1)$, making it possible to generate an indicator of surveillance of the level of cavitation at the next micro-interruption $M_C(2)$, from the moment that the level of amplitude, that is to say the intensity of the radiation force generated in the focal zone, exceeds a certain threshold.

According to another embodiment, the measurement of the level of cavitation may be generated automatically at each micro-interruption.

In the example of FIG. 4, at the end of the second micro-interruption $M_C(2)$, if the measurements of elasticity of the tissue indicate that the tissue still has elastic properties beyond a certain threshold by means of the calculations carried out by the computer K, then the ablation is not finished. In this case, the process of ablation generates, GEN $F_{US}$, a third beam of ultrasound signals $F_{US}$ of amplitude $A_3$ and of duration $D_3$ after the end of the micro-interruption $M_C(2)$. The levels of amplitude $A_3$ and duration $D_3$ may be estimated to finalise the ablation at the end of this third beam.

This operation may be renewed up to a threshold of level of elasticity of the tissues is calculated. In this case, the process of ablation of the targeted zone $Z_C$ can end.

Throughout the ablation process, a control of the position of the beam on the targeted zone has been carried out. In FIG. 4, cut offs of the beam when contraction movements of the heart are taken into account to activate or deactivate the beam are not represented for example. In this specific case, it is assumed that the phased array RES_US is constantly controlled on the movements of the heart, of which respiratory movements and contraction movements.

The invention claimed is:

1. A method for controlling a focussed signal for its application in a targeted zone of a heart in order to generate a lesion only in the targeted zone, the method comprising:
   acquiring at least one frequency of an electrocardiogram of the heart;
   acquiring at least one image of a region of the heart in which the targeted zone is located, said at least one image being acquired in synchronisation with the frequency acquired from the electrocardiogram of the heart, by a single MRI imaging system;
   generating, during a QT period of the electrocardiogram, a first beam of focussed ultrasound signals in the targeted zone, said first beam being emitted by a phased array, said ultrasound signals being configured in phase to generate at least one pulse in a focussed zone within the targeted zone, said at least one pulse being synchronised with the frequency acquired from the electrocardiogram of the heart, the at least one pulse having a predefined amplitude and duration;
   during the generating, performing a dynamic control of a position of the focussed zone on a position of the targeted zone by a positioning system comprising the single MRI imaging system so as to measure displacements of the targeted zone of the heart in a reference frame linked to the phased array, the displacements of the targeted zone being measured by measuring respiratory movements of the heart in the reference frame linked to the phased array using said positioning system and by measuring contraction movements of the heart in the reference frame linked to the phased array using said positioning system and to deduce therefrom a compensation parameter to calculate a new position of the targeted zone and control deflection of the first beam, said phased array automatically applying a phase parameter to each signal to deflect the first beam to the new position of the targeted zone; and
   performing an active and dynamic monitoring of a temperature and/or a tissue deformation near to and/or in the focussed zone from an acquisition of at least one image of said zone by the single MRI imaging system, and of a level of cavitation at a level of the focussed zone by an ultrasound device that detects a spectrum of ultrasound frequencies in or near to the focussed zone, the level of cavitation being deduced from a spectral noise level of the spectrum,
   the amplitude and/or the duration of the at least one pulse being adjusted dynamically as a function of the monitored temperature and/or tissue deformation and level of cavitation,
      wherein the method further comprises, in a zone of the heart neighbouring the focussed zone:
         measuring the level of cavitation to determine a measured level of cavitation and comparing said measured level of cavitation with a first threshold;
         measuring the tissue deformation to determine a measured tissue deformation and comparing the measured tissue deformation with a second threshold, and
         cutting off the first beam of focussed ultrasound signals when both the first and second thresholds are exceeded.

2. The method according to claim 1, the tissue deformation near to and/or in the focussed zone is determined in response to at least one pulse of the first beam.

3. The method according to claim 1, further comprising:
   determining an image of a transcostal wall projected in an image plane of the phased array by taking into consideration a position and a direction of the phased array;
   a deactivation of elements of the phased array in accordance with the position of said elements with regard to a position of the projected image of the transcostal wall.

4. The method according to claim 1, further comprising:
   performing a dynamic control of the deactivation and the activation of elements of the phased array as a function of a calculation of each phase parameter applied to each of the signals.

5. The method according to claim 1, wherein data acquired by the single MRI imaging system are utilized to deduce a local tissue deformation induced by the ultrasound pressure generated by the first beam of ultrasound signals and a local rise in temperature induced by an energy generated locally by the beam of ultrasound signals.

6. The method according to claim 1, wherein a comparison of the position of the focussed zone and the position of the targeted zone determined by the positioning system, generates at least one data for calibrating elements of the phased array so as to make a position of the focussed zone correspond with the position of the targeted zone.

7. The method according to claim 1, wherein the positioning system further comprises at least one emitter emitting ultrasound waves and a plurality of ultrasound sensors detecting reflected waves, the position being determined by triangulation.

8. The method according to claim 1, further comprising calibrating a signal generated in the focussed zone by defining parameters comprising at least one level of the amplitude and a pulse duration as a function of at least one data among which:
   a temperature set point in the focussed zone and/or in neighbouring zones and/or in the ribs of the transcostal wall;

a tissue deformation set point in the focussed zone, and/or;

a level of cavitation set point in the focussed zone, and/or;

a detection of movement of the focussed zone in a reference point linked to the phased array, and/or;

an electrical activity set point in the focussed zone.

9. The method according to claim 1, wherein the steps of the monitoring method are carried out in different targeted zones of the heart, the method further comprising, after the application of a beam of focussed signals:

verifying different values representing either tissue deformations of each targeted zone ($Z_C$), or electrical levels measured near to or in each targeted zone, said measured values being compared to given thresholds.

10. A method for controlling a focussed signal for its application in a targeted zone of a heart in order to generate a lesion only in the targeted zone, the method comprising:

acquiring at least one frequency of an electrocardiogram of the heart;

acquiring at least one image of a region of the heart in which the targeted zone is located, said at least one image being acquired in synchronisation with the frequency acquired from the electrocardiogram of the heart, by a single MRI imaging system;

generating, during a QT period of the electrocardiogram, a first beam of focussed ultrasound signals in the targeted zone, said first beam being emitted by a phased array, said ultrasound signals being configured in phase to generate at least one pulse in a focussed zone within the targeted zone, said at least one pulse being synchronised with the frequency acquired from the electrocardiogram of the heart, the at least one pulse having a predefined amplitude and duration;

during the generating, performing a dynamic control of a position of the focussed zone on a position of the targeted zone by a positioning system comprising the single MRI imaging system so as to measure displacements of the targeted zone induced by respiratory movements of the heart and contraction movements of the heart, said displacements of the targeted zone of the heart induced by the respiratory movements of the heart and the contraction movements of the heart being measured by the positioning system in a reference frame linked to the phased array, wherein a compensation parameter is deduced from measurements of said displacements to calculate a new position of the targeted zone and control deflection of the first beam, said phased array automatically applying a phase parameter to each signal to deflect the first beam to the new position of the targeted zone; and performing an active and dynamic monitoring of a temperature and/or a tissue deformation near to and/or in the focussed zone from an acquisition of at least one image of said zone by the single MRI imaging system, and of a level of cavitation at a level of the focussed zone by an ultrasound device that detects a spectrum of ultrasound frequencies in or near to the focussed zone, the level of cavitation being deduced from a spectral noise level of the spectrum, the amplitude and/or the duration of the at least one pulse being adjusted dynamically as a function of the monitored temperature and/or tissue deformation and level of cavitation, wherein the method further comprises, in a zone of the heart neighbouring the focussed zone:

measuring the level of cavitation to determine a measured level of cavitation and comparing said measured level of cavitation with a first threshold;

measuring the tissue deformation to determine a measured tissue deformation and comparing the measured tissue deformation with a second threshold, and cutting off the first beam of focussed ultrasound signals when both the first and second thresholds are exceeded.

* * * * *